United States Patent [19]

Higa

[11] Patent Number: 4,985,255

[45] Date of Patent: Jan. 15, 1991

[54] EXTERNAL PREPARATIONS OF MELANOGENESIS-INHIBITORY AGENT

[75] Inventor: Yoshitaka Higa, Dazaifu, Japan

[73] Assignee: Sansho Seiyaku Co., Ltd., Fukuoka, Japan

[21] Appl. No.: 182,621

[22] Filed: Apr. 18, 1988

[51] Int. Cl.$^5$ .................... A61K 35/50; A61K 31/35
[52] U.S. Cl. .................................... 424/583; 514/460
[58] Field of Search .................... 424/105, 95, 583; 514/460

[56] References Cited

PUBLICATIONS

Higa, cited in Chem. Abstracts, vol. 104:74818k, (1986).
Ichimaru Farukosu KK, cited in Chem. Abstracts, vol. 100:39578c, (1984).
Nagai et al., cited in Chem. Abstracts, vol. 96:11515e, (1982).

*Primary Examiner*—Jacqueline Stone
*Attorney, Agent, or Firm*—Jordan and Hamburg

[57] ABSTRACT

External preparations of 1 melanogenesisinhibitory agent contain, as active ingredients, a placental extract of pregnant cows and kojic acid or a derivative thereof. The placental extract of pregnant cows is a very effective melanogenesis-inhibitory substance, which acts through a mechanism different from that of the known extract of fully-matured human placenta and markedly diminishes the overall activity of tyrosinase isozymes ($T_1$, $T_2$ and $T_3$). The external preparations, which utilize the synergistic effect between this unique substance and kojic acid or a derivative thereof (a known melanogenesis-inhibitory substance), are effective for the relief and prevention of pigmentation diseases, such as liver spots.

2 Claims, 2 Drawing Sheets

Tyrosinase isozyme activity

Placental Extract of Pregnant Cow

Tyrosinase isozyme activity

Fully-matured Human Placenta Extract

EXTERNAL PREPARATIONS OF MELANOGENESIS-INHIBITORY AGENT

BACKGROUND OF THE INVENTION

1. Field of the Invention

This invention relates to external preparations containing, as active ingredients, a placental extract of pregnant cows and kojic acid or a derivative thereof.

2. Description of the Prior Art

Peroxides, such as hydrogen peroxide, magnesium peroxide, sodium peroxide and zinc perborate, had long been used as the active ingredient in the so-called bleach-mask cosmetics, that is, cosmetics to make the human skin fair. But these peroxides, which are very unstable compounds, were poor in storage stability, had difficulty in formulation together with base materials, and were not satisfactory in the intended effect. Cosmetics containing vitamin C, cystein or colloidal sulfur were later introduced for the same purpose, but the effect of these cosmetics was also unsatisfactory. Besides these, are also known bleach-mask cosmetics using kojic acid (Japanese Patent Publication No. 5618569), and bleach-mask cosmetics using kojic acid derivatives (Japanese Patent Kokai No. 56-79616, No. 567710, No. 56-7776 and No. 59-33207). Cosmetics using a placental extract are also known (Japanese Patent Publication No. 35-15399). In addition, bleach-mask cosmetics using a placental extract (from a fullymatured human placenta, for example) and kojic acid or a derivative thereof have also been disclosed (Japanese Patent Kokai No. 61-202806).

SUMMARY OF THE INVENTION

The object of this invention is to provide external preparations employing a placental extract of pregnant cows which differs from a fully-matured human placenta extract in working mechanism and exceeds in effect as a melanogenesis-inhibitory agent and kojic acid or a derivative thereof, that is better than conventional preparations.

Intensive studies on this subject have led us to find that this object can be achieved by utilizing the synergistic effect between a placental extract of pregnant cows and kojic acid or a derivative thereof. An external preparation containing a placental extract of pregnant cows and kojic acid or a derivative thereof showed an outstanding effect against melanin formation in a test on B16 cells derived from mouse melanoma and in a clinical test. This invention was accomplished on the basis of these findings.

Thus, this invention relates to external preparations containing, as active ingredients, a placental extract of pregnant cows and kojic acid or a derivative thereof.

DESCRIPTION OF THE PREFERRED EMBODIMENTS

The placental extract of pregnant cows used in this invention is an aqueous solution, or a freeze-dried product thereof, which is obtained by taking out the placenta from a pregnant cow, washing it with water, removing the blood, chopping the washed placenta into small pieces (the resulting debris may be stored in frozen state, when desired), extracting the soluble debris thus obtained with water, and removing impurities from the aqueous extract.

Extraction can be effected, for example, according to the following procedure: cutting the placenta into small pieces, followed by removal of the blood; mechanically disrupting the cut pieces by means of a mixer or the like; and extracting the debris thus obtained with water at about 40° to 45° C. for 3 to 5 hours, followed by centrifugal separation. The crude placental extract is adjusted to pH of 6.4 to 5 and heated at 50° to 60° C. for about 10 minutes, the precipitate which separates out is filtered off through a sheet of filter paper, and the filtrate is adjusted to pH 6.0 to 7.5.

MANUFACTURING EXAMPLE

Placentas of pregnant cows were washed with water, cut into pieces about 1 cm square, squeezed in water to remove the blood, and dewatered thoroughly. The pieces thus treated (40.00 Kg) were further cut into smaller fragments, 80.0 liters of pure water and 240 g of methyl p-oxybenzoate were added, the mixture was treated in a mixer, and the pulpy suspension thus formed was heated at 40° to 45° C. for three hours with gentle stirring to effect extraction. The extract thus obtained was centrifuged at 8000 rpm, the supernantant collected was adjusted to pH 4.5 and heated at 50° C. for ten minutes with stirring to precipitate proteins having isoelectric points at this pH, which were filtered off through a sheet of filter paper. The filtrate was adjusted to pH 7.0 by addition of 10% caustic soda solution, and the mixture was again filtered, giving 80 Kg of placental extract.

Figure 1:
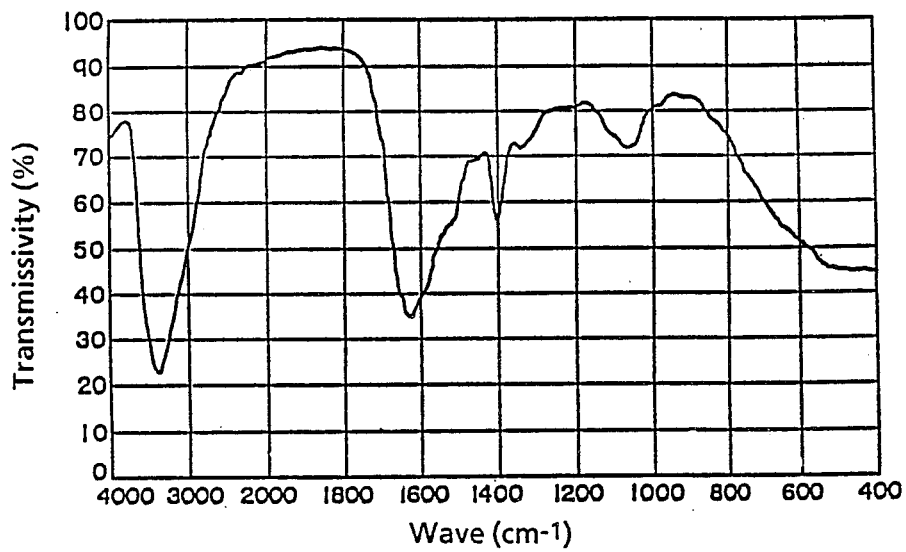
FIG. 1 is the infrared absorption spectrum of the placental extract of pregnant cows, which is an active ingredient of the external preparations of this invention.
Figure 2:
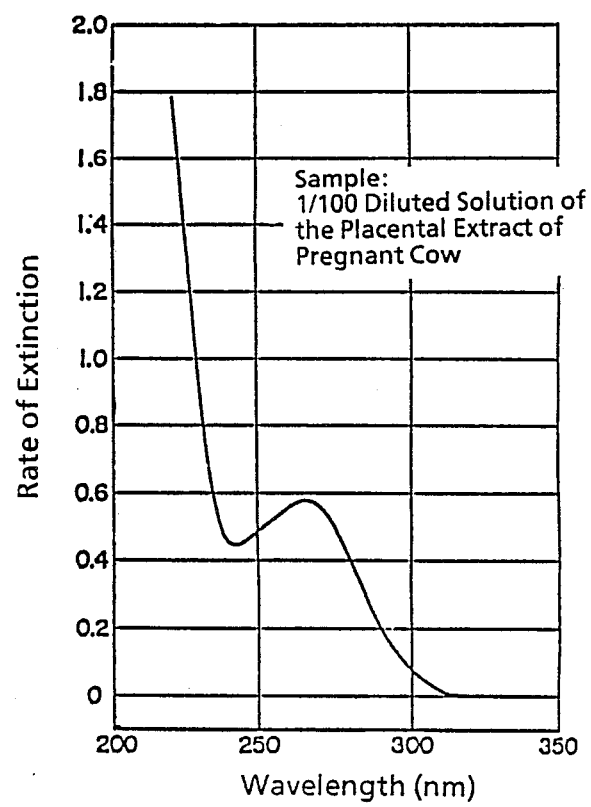
FIG. 2 is the ultraviolet absorption spectrum of the same.

The placental extract of pregnant cows thus obtained shows unique melanogenesis-inhibitory action different in working mechanism from that of the known extract of fully-matured human placenta. It is a melanogenesis-inhibitory substance with a nitrogen content of 105 mg/100 ml and having IR and UV absorption spectra as shown in FIGS. 1 and 2, respectively.

Tests on its melanogenesis-inhibitory action and the results obtained are described below. (Test on Melanogenesis-inhibitory Action)

The placental extract of pregnant cows prepared in the above Manufacturing Example was dissolved in Eagle's MEM medium containing 10% fetal bovine serum, and B16 mouse melanoma cells (hereinafter abbreviated as B16 cells) were grown in this culture medium. After five days of culture, the cells lost color almost completely. Observation of these color-faded B16 cells under an optical microscope revealed a decreased number of cells positive to the dopa reaction and to the premelanosome reaction, while electron-microscopic observation showed a markedly decreased number of melanin-developed melanosomes and a large number of morphologically changed premelanosomes. In a recovery test, in which the color-faded cells were cultured in a medium not containing the placental extract of pregnant cow for five days, premelanosome recovered favorably as observed under an electron microscope, and was restored completely after five days.

The tyrosinase isozyme activity of the above B16 cells cultured on a medium containing the placental extract of pregnant cow gradually diminished during the culture period. The tyrosinase isozyme activity in electrophoresis diminished for all the types of isozyme, $T_1$, $T_2$ and $T_3$.

Tyrosinase is an important enzyme participating in the formation of melanin and is present in living bodies as three types of isozyme, $T_1$, $T_2$ and $T_3$. It is first created as type-$T_2$ isozyme, then modified to type $T_1$ and to type $T_3$ in that order, and finally present in granules in which melanin is formed (premelanosomes) as type $T_3$.

As described above, the melanogenesis-inhibitory action of the placental extract of pregnant cow is characterized by the activity of tyrosinase activity generally diminishing with the passage of time for all of the types, $T_1$, $T_2$ and $T_3$.

On the other hand, a similar test was conducted on the melanogenesis-inhibitory action of the known extract of fully-matured human placenta against B16 cells by the same method as above. Electron-microscopic observation showed a decreased number of premelanosomes. The test of tyrosinase activity of B16 cells cultured in a medium containing the above extract revealed a sharp decrease in the activity of type-$T_2$ isozyme in the earlier stage of cultivation, followed by a decrease in the activity of isozymes $T_1$ and $T_3$ in the later stage.

Figure 3:
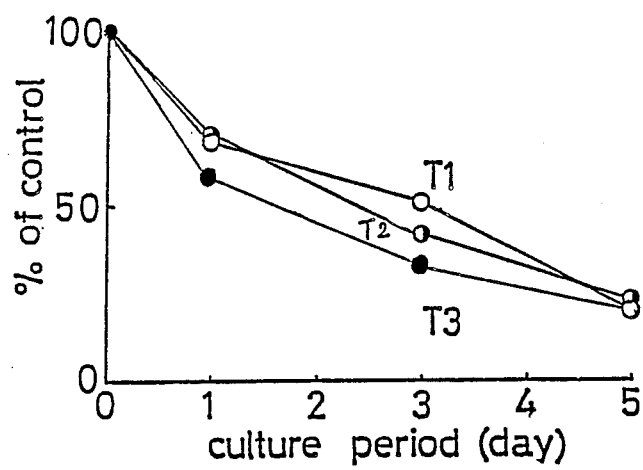
FIG. 3 is a graph illustrating the tyrosinase isozyme activity of the same.
Figure 4:
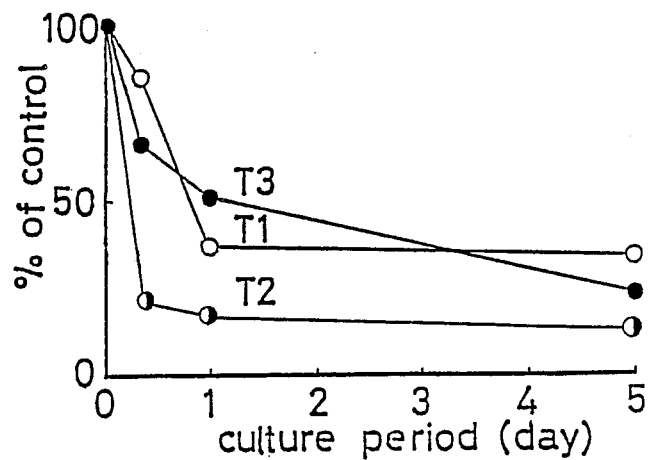
FIG. 4 is a graph illustrating the tyrosinase isozyme activity of an extract of fully-matured human placenta.

These test results are shown in FIG. 3 (placental extract of pregnant cows) and in FIG. 4 (extract of fully-matured human placenta).

It is clear from the above results that a placental extract of pregnant cows and a per se known extract of fully-matured human placenta are distinct from each other in the melanogenesis-inhibitory action.

Examples of the kojic acid derivatives used in this invention, includes its fatty acid monoesters such as kojic acid monocaprylate and kojic acid monostearate (Japanese Patent Kokai No. 56-77272); its fatty acid diesters such as kojic acid dipalmitate, kojic acid dioleate and kojic acid distearate (Japanese Patent Kokai No. 56-7776); and other types of esters such as kojic acid monocinnamate and kojic acid monobenzoate (Japanese Patent Kokai No. 59-33207).

The mixing ratio of the placental extract of pregnant cows to kojic acid or a derivative thereof is most preferably such that the amount of the latter is 1 to 30% based on the weight of the former.

The sufficient amounts of these two active ingredients to be contained in the external preparations of this invention are in the range from 0.1 to 10 weight % and in the range from 0.1 to 3 weight %, respectively.

The external preparations of this invention are principally applied in the form of emulsions, lotions and ointment, but may also be used as cosmetics, such as lotions, emulsions, cream and packs. These may be prepared by commonly employed methods using ordinary bases and additives.

Described below are test examples to show the melanogenesis-inhibitory action of the external preparations of this invention.

(1) Test using B16 cells

B16 cells were added to each of the media listed below and cultured for six days.

(Zone A-I) A medium containing ⅛ the volume of the placental extract of pregnant cows prepared in Manufacturing Example (Zone A-II) A medium containing 0.5 mM kojic acid (Zone A-III) A medium containing 0.5 mM kojic acid and ⅛ the volume of the placental extract of pregnant cows prepared in Manufacturing Example (Zone A-IV) A medium containing ¼ the volume of the placental extract of pregnant cows prepared in Manufacturing Example (Zone A-V) A medium containing 1.0 mM kojic acid (Zone A-VI) A medium containing 1.0 mM kojic acid and ¼ the volume of the placental extract of pregnant cows prepared in Manufacturing Example The grown cells in each zone were dispersed by the addition of trypsin and collected by centrifugation (1000 rpm × 5 minutes), and the degree of melanism was visually judged. The result is shown in Table 1.

TABLE 1

| Test Zone | A-I | A-II | A-III | A-IV | A-V | A-VI |
|---|---|---|---|---|---|---|
| Degree of melanism | ± | ± | +++ | ±~+ | ±~+ | +++ |

−: Black (control), ±: Slightly faded
+: Moderately faded, ++: Considerably faded
+++: Decolorized almost completely The above test results clearly show that the external preparations of this invention are highly effective in fading the color of B16 melanoma cells.

Melanin formation is considered to follow the steps of Tyrosine → DOPA → Dopaquinone Dopachrome → Melanin, in which tyrosinase participates in the reactions of Tyrosine → DOPA → Dopaquinone. Kojic acid and derivatives thereof retard the action of tyrosinase, and the placental extract of pregnant cow retard the formation of tyrosinase in cells, thereby inhibiting melanogenesis. In this way, the two kinds of active ingredients in the external preparations of this invention synergistically inhibit melanin formation through different working mechanisms.

(2) Coating test on human skin

A coating test was conducted at three hospitals (A, B and C) on patients suffering from liver spots (25 persons in each) using the ointment of this invention.

Final evaluation was made on the basis of visual observation three months later. The result is as shown below.

(Evaluation standard)
Ineffective: No color fading observed
Slightly effective: Slight color fading
Effective: Apparent color fading
Markedly effective: Complete or almost complete cure (Test result)
In total 75 patients;
"Ineffective": 6 patients,
"Slightly effective": 18 patients,
"Effective": 36 patients,
"Markedly effective": 15 patients.
Sum of "Slightly effective", "Effective" and "Markedly effective": 69 patients (Efficacy rate: 92%).

As is apparent from the foregoing, the placental extract of pregnant cows contained in the external preparations of this invention as an active ingredient is a very effective melanogenesis-inhibitory substance, which acts through a mechanism different from that of the known extract of fully-matured human placenta and markedly diminishes the overall activity of tyrosinase isozymes ($T_1$, $T_2$ and $T_3$) that are enzymes essential to the formation of melanin in living bodies. The external preparations of this invention, which utilize the synergistic effect between this unique substance and kojic acid or a derivative thereof (a known melanogenesis-inhibitory substance), are effective for prohibiting remarkably generation of melanin and preventing pigmentation diseases, such as liver spots by application of the external preparation of this invention to the affected part.

EXAMPLE 1 (OINTMENT)

A mixture of 2.00 g polyethylene glycol (40 E.O.) monostearate, 5.00 g self-emulsifiable glycerol monostearate, 5.00 g stearic acid, 1.00 g behenyl alcohol, 10.00 g liquid paraffin, 10.00 g glycerol trioctanoate and 0.20 g methyl p-oxybenzoate was heated until clear. To this solution, was added a heated solution of 5.00 g 1,3-butylene glycol and 48.80 g pure water with stirring to effect emulsification. After cooling, 1.0 g kojic acid and 6.0 g placental extract of pregnant cows were added to the emulsion, and the mixture was stirred well, cooled and charged in suitable containers.

EXAMPLE 2 (EMULSION)

A mixture of 1.00 g polyoxyethylene-sorbitan(20 E.O.) monostearate, 0.50 g polyoxyethylene-sorbitan (60 E.O.) tetraoleate, 1.00 g lipophilic glycerol monostearate, 0.50 g stearic acid, 0.50 g behenyl alcohol, 4.00 g avocado oil, 4.00 g glycerol trioctanoate and 0.20 g methyl p-oxybenzoate was heated until clear. To this solution, was added a heated solution of 5.00 g 1,3-butylene glycol, 0.14 g xanthan gum, 0.5 g kojic acid, 4.0 g placental extract of pregnant cows and 76.16 g pure water with stirring to effect emulsification. After cooling, a small amount of perfume was added to the emulsion, and the mixture was stirred well, cooled and charged in suitable containers.

EXAMPLE 3 (LOTION)

Pure water was added to a mixture of 0.2 g kojic acid, 5.0 g placental extract of pregnant cows, 0.10 g methyl p-oxybenzoate, 0.01 g hyaluronic acid and a small amount of perfume to make up a total weight of 100 g, and the resulting mixture was stirred well and charged in a suitable container.

The external preparations of this invention may be applied at suitable doses depending on the conditions of the affected part, and are preferably coated on the affected part three times a day after washing.

What is claimed is:

1. An external preparation of a melanogenesisinhibitory agent comprising, as active ingredients, a placental extract of pregnant cows and kojic acid or a derivative thereof.

2. The external preparation of a melanogenesisinhibitory agent as defined in claim 1 wherein the amount of said kojic acid or a derivative thereof is 1 to 30% based on the weight of said placental extract of pregnant cows and the sum of these two active ingredients is 0.1 to 3% based on the total weight of said external preparation.

* * * * *